(12) United States Patent
Laguette et al.

(10) Patent No.: US 6,478,821 B1
(45) Date of Patent: Nov. 12, 2002

(54) IRIS FIXATED INTRAOCULAR LENS AND METHOD OF IMPLANTATION

(75) Inventors: Stephen W. Laguette, Santa Barbara, CA (US); Joseph I. Weinschenk, III, Laguna Niguel, CA (US)

(73) Assignee: Advanced Medical Optics, Inc., Santa Ana, CA (US)

( * ) Notice: Subject to any disclaimer, the term of this patent is extended or adjusted under 35 U.S.C. 154(b) by 0 days.

(21) Appl. No.: 09/484,126

(22) Filed: Jan. 12, 2000

(51) Int. Cl.[7] .................................................. A61F 2/16
(52) U.S. Cl. ...................... 623/6.49; 623/6.56; 623/6.59
(58) Field of Search ...................... 623/6.18, 6.38–6.56, 623/6.59

(56) References Cited

U.S. PATENT DOCUMENTS

| | | |
|---|---|---|
| 3,866,249 A | 2/1975 | Flom |
| 3,986,214 A | 10/1976 | Krasnov |
| 4,159,546 A | 7/1979 | Shearing |
| 4,206,518 A * | 6/1980 | Jardon et al. ............... 623/6.44 |
| 4,215,440 A | 8/1980 | Worst |
| 4,262,370 A | 4/1981 | Hartstein |
| 4,316,293 A | 2/1982 | Bayer |
| 4,370,760 A | 2/1983 | Kelman |
| 4,403,354 A | 9/1983 | Rainin |
| 4,404,694 A | 9/1983 | Kelman |
| 4,409,690 A | 10/1983 | Gess |
| 4,435,855 A | 3/1984 | Pannu |
| 4,542,540 A | 9/1985 | White |
| 4,542,541 A | 9/1985 | Pannu |
| 4,551,864 A | 11/1985 | Akhavi |
| 4,560,383 A | 12/1985 | Leiski |
| 4,687,484 A | 8/1987 | Kaplan |
| RE32,525 E | 10/1987 | Pannu |
| 5,047,052 A | 9/1991 | Dubroff |
| 5,071,432 A | 12/1991 | Baikoff |
| 5,147,397 A | 9/1992 | Christ et al. |
| 5,192,319 A | 3/1993 | Worst |
| 5,225,858 A | 7/1993 | Portney |
| 5,567,365 A | 10/1996 | Weinschenk, III et al. |
| 5,628,796 A | 5/1997 | Suzuki |
| 5,766,244 A | 6/1998 | Binder |

FOREIGN PATENT DOCUMENTS

| | | | |
|---|---|---|---|
| DE | 2437184 | 2/1975 | |
| FR | 2757065 | 12/1996 | |
| RU | 2106126 C1 * | 3/1998 | ........ 623/FOR 105 |
| RU | 2132172 C1 * | 6/1999 | ........ 623/FOR 105 |
| WO | 9727825 | 8/1997 | |

* cited by examiner

*Primary Examiner*—David H. Willse
(74) *Attorney, Agent, or Firm*—Frank J. Uxa, Jr.; Peter Jon Gluck

(57) ABSTRACT

Iris fixated intraocular lenses include an optic and at least one fixation member or haptic. The fixation member is joined to the optic and has a distal segment including a through-iris portion adapted to extend through an iris hole, and an anchor portion. The anchor portion has or is adapted to have an anchor structure positioned to be disposed proximate to a side of the iris so as to be a effective in fixating the intraocular lens to the iris. The anchor structure may be formed prior to inserting the intraocular lens in the eye or may be formed after the intraocular lens is inserted in the eye. Methods for inserting such intraocular lenses in the eye are also provided.

10 Claims, 5 Drawing Sheets

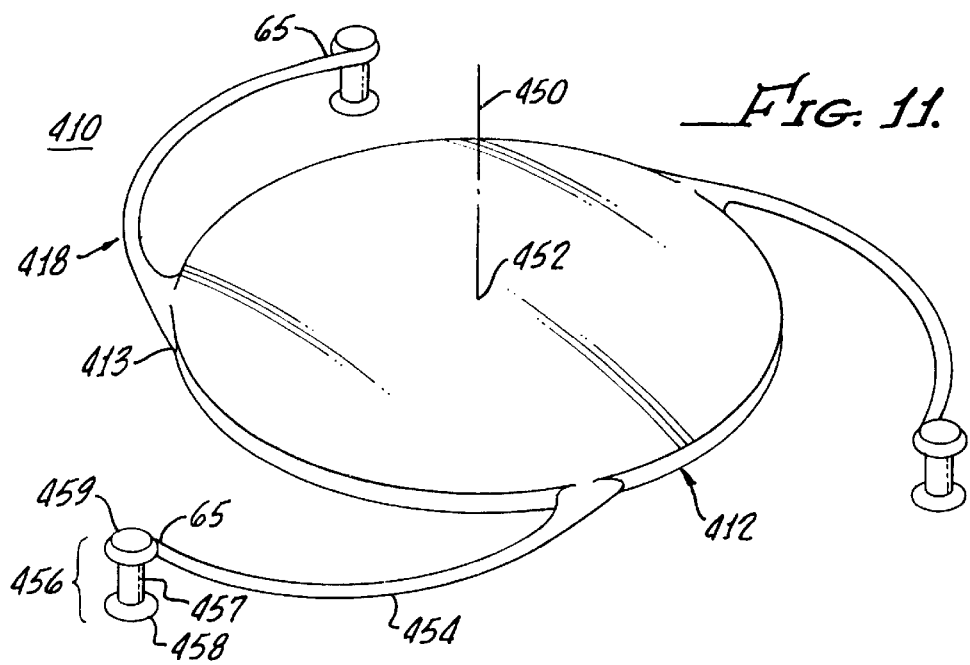
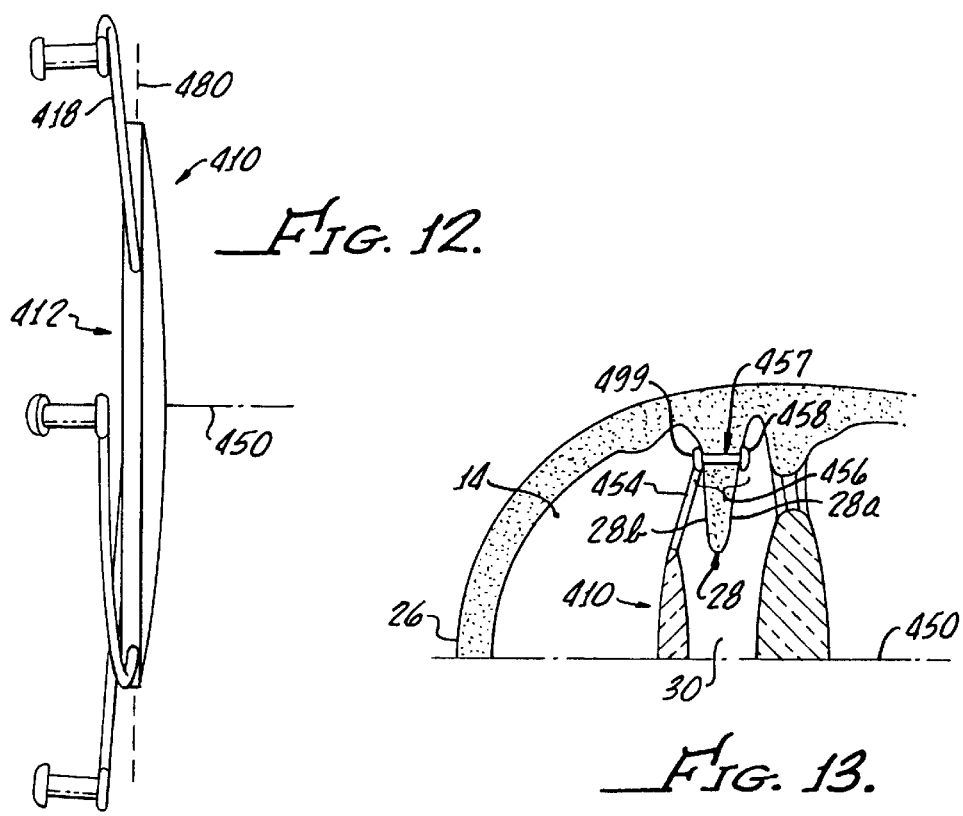

IRIS FIXATED INTRAOCULAR LENS AND METHOD OF IMPLANTATION

BACKGROUND OF THE INVENTION

This invention relates to intraocular lenses (IOLs) and in particular to IOLs that reduce or even eliminate irritation of the ciliary band or angle and the sulcus in the eye and reduce the incidence of pupillary block, and, if a natural crystalline lens is present, to reduce the risk of cataract formation.

IOLs are commonly used to modify vision. For example, IOLs are used to replace the natural lens of the eye when warranted by medical conditions. A common practice is to implant an IOL in a region of the eye known as the capsular bag or posterior bag or capsule. However, in this practice, a potential risk exists that cells from the eye may grow in front of and/or in back of the optical portion of the IOL. Such cell growth tends to block the optical portion of the IOL and impair vision.

IOLs may be implanted in regions of the eye other than in the capsular bag. Anterior chamber IOLs (AIOLs) and posterior chamber IOLs (PIOLs) are known in the prior art. These prior art IOLs are designed such that a portion of the haptics of the IOLs are located against the angle or ciliary band of the eye for the AIOLs or against the sulcus of the eye for the PIOLs.

A disadvantage of the prior art AIOLs is the risk that the fixation members or haptics of the AIOLs may irritate the ciliary band. A disadvantage of the PIOLs is the risk that the optic of the PIOLs may irritate the natural crystalline lens, if such lens is present, and possibly result in cataract formation.

Referring now to Prior Art FIG. 1, a posterior/anterior chamber intraocular lens ("PACL") 10 combines the advantage of an optic 12 positioned in the anterior chamber 14 of an eye 16 and haptics 18 that position the lens resting in the sulcus 20. The PACL 10 reduces the opportunity of irritation to the angle or ciliary band 22 and the natural lens 24. Such PACLs are disclosed in U.S. patent application Ser. No. 09/166,328 filed Oct. 5, 1998, which is commonly assigned with the present application and is incorporated herein in its entirety by reference.

The eye 16 is comprised of a cornea 26 shown to the left and an iris 28 shown in the middle of the eye. It is to be understood that the cornea 26 is at the front of the eye 16. The iris 28 divides the eye 16 into the anterior chamber 14 at the front of the eye and the posterior chamber 30 in the back of the eye. The iris 28 also defines the pupil 32, which is the opening in the middle of the iris. In front of the iris 28 is the sclera spur 34. The sclera spur 34 and the iris 28 delimit the ciliary band 22. Behind the iris 28 is the ciliary process 36, from which extends the ciliary muscle 38. The ciliary muscle 38 supports the natural crystalline lens 24 of the eye 16. The iris 28 and the ciliary process 36 define the sulcus 20.

The haptics 18 of the PACL 10 are two opposing elongated fixation members that extend from the optic 12. The optic 12 defines an optical axis 50 that extends through the center 52 of the optic. The haptics 18 have a proximal segment 54 attached to the optic 12, an intermediate segment 56, and terminates in a distal segment 58. The optic 12 and the proximal segment 54 are located in the eye anterior chamber 14. The haptic distal segment 58 rests against the sulcus 20.

The intermediate segment 56 of the haptic 18 extends through a hole 60 in the periphery of the iris 28. The intermediate segment 56 is substantially parallel to the optical axis 50. The holes 60 may be formed by an iridectomy, or be naturally occurring openings in the iris 28. The holes 60 have an additional benefit of improving fluid flow between the anterior chamber 14 and the posterior chamber 30. Other details of the PACL 10 are disclosed in the above-incorporated U.S. Patent Application.

Recently developed AIOLs for insertion in eyes which contain the natural crystalline lens ("phakic" eyes) include the Nuvita™ MA-20 lens, which has a four-point haptic for fixation in the angle, and is made of rigid polymethyl methacrylate (PMMA). Another AIOL used in phakic eyes is known as the Artisan™ lens and is disclosed in Worst U.S. Pat. No. 5,192,319, which is incorporated in its entirety herein by reference. This AIOL is fixated on the iris by "pinching" the iris tissue. Made of rigid PMMA, the Artisan™ lens is difficult to implant due to the delicacy of the iris tissue. Worst U.S. Pat. No. 4,215,440, which is incorporated in its entirety herein by reference, discloses another iris-fixated AIOL, which uses one or more fixation members, each having a pair of pincer arms that pinch an anterior surface of the iris. This AIOL detachably attaches the IOL to the iris such that the optic is positioned in the iris opening and has many of the same disadvantages as does the Artisan™ lens. Suzuki U.S. Pat. No. 5,628,796, which is incorporated in its entirety herein by reference, discloses an AIOL with fixation arms or support legs that are inserted in and through fine bores or apertures made by incision in a peripheral site of the iris.

Disadvantages associated with these IOLs for phakic implantation include a requirement for large incisions in the cornea for non-foldable IOLs and potential for damage and inflammation to delicate tissue from rigid haptics. Also involved are one or more of the complications which include corneal endothelial cell loss due to mechanical abrasion against the cornea, inflammation, pupil ovalization, problems with aqueous flow in the iridio-corneal angle, and implant decentration.

There continues to be a need for new IOLs.

SUMMARY OF THE INVENTION

New iris fixated intraocular lenses (IFIOLS) have been discovered. The present IFIOLs are relatively easy and straightforward to implant in the eye and effectively fixate to the iris of the eye. The present IFIOLs are adapted to be firmly fixated to the iris, for example, so as to prevent accidental dislodgement. These IFIOLs can be sized and structured so as not to interfere with the zonules and sulcus angle of the eye, and with the natural lens of the eye, if such natural lens is present.

The iris to which the present IFIOL is fixated has a side and a hole, for example, a iridectomy hole or opening, extending from the iris side and through the iris. In one broad aspect, the present IFIOLs comprise an optic and at least one fixation member or haptic. The fixation member is joined to the optic and includes a distal segment including a through-iris portion adapted to extend through the iris hole and an anchor portion. The anchor portion has or is adapted to have an anchor structure positioned to be disposed proximate to the iris side so as to be effective in fixating the IFIOL to the iris.

In one aspect of the invention, the optic is adapted to be disposed in the anterior chamber while the anchor portion is adapted to be disposed in the posterior chamber or the anterior chamber, preferably in the posterior chamber.

The anchor portion may have the anchor structure prior to the intraocular lens being placed in the eye or the anchor portion may be adapted to form the anchor structure after the intraocular lens is placed in the eye.

In one embodiment, the anchor portion adapted to form the anchor structure after insertion or placement in the eye may be comprised of hydrophilic material adapted to absorb aqueous fluid and form the anchor structure in the eye. The hydrophilic material used may be any suitable such material, for example, a material suitable for use in the eye. Examples of useful hydrophilic materials include, but are not limited to, acid-treated polymers, base-treated polymers, hydrogel-forming polymeric materials and the like and mixtures and combinations thereof.

In another embodiment of the invention, the anchor portion adapted to form the anchor structure after insertion in the eye may be comprised of an elastic memory material adapted to form the anchor structure in the eye. Any suitable elastic memory material may be employed, provided that such material is useful in the eye and can be treated in the eye to form the anchor structure at conditions which do not detrimentally affect the eye. Examples of useful elastic memory materials are well known in the art.

In one embodiment, the anchor structure has a transverse cross-sectional area that is larger than a transverse cross-sectional area of the through-iris portion of the fixation member. Also, the through-iris portion may, and preferably does, have a longitudinal axis oriented in a direction other than normal to an optical axis of the optic.

The IFIOLs of the invention may have at least three fixation members, for example, three or four fixation members, but may also have any number of such members. Further, not all of the fixation members need be adapted to fixate to the iris.

In one particularly useful embodiment, fixation member or members include a plate, or plate-like, element joined to the optic. Such plate elements have been found to effectively facilitate fixating the present IFIOLs to the iris. For example, the plate elements are effective in reducing, or even substantially eliminating, movement of the optic in the eye which can disadvantageously cause vision distortion. One important feature of these plate elements is in facilitating the placement of the IFIOLs in the eye. Thus, the relatively large and strong plate elements provide a degree of structural rigidity and are adapted to facilitate passing the distal segments of the fixation members into and through the holes in the iris. Such facilitation increases the ease with which the IOL is installed in the eye and, thereby advantageously, reduces patient trauma and/or surgeon stress.

In one aspect of the invention, the distal segment of the fixation member includes an other or an additional anchor portion having or adapted to have an other or an additional anchor structure. In this aspect, the first anchor portion is adapted to be disposed on one side of the iris, the second anchor portion preferably is adapted to be disposed on the other side of the iris, and the through-iris portion of the distal segment extends through the iris hole and between the two anchor portions. One or both of the two anchor structures may be formed prior to insertion of the IFIOL into the eye or may be formed after the IFIOL is placed in the eye. One of the anchor structures preferably is adapted to be disposed in the posterior chamber while the other anchor structure preferably is adapted to be disposed in the anterior chamber. In a very useful embodiment, the anchor structure is adapted to be formed after the IFIOL is placed in the eye and the other anchor structure is adapted to be present prior to the intraocular lens being placed in the eye. The two anchor structures may have substantially the same or different configurations.

In one embodiment, one or both of the anchor portion and the other anchor portion are adapted to enlarge in the eye and form an anchor structure, or comprise an elastic memory material adapted to form an anchor structure in the eye, or have a transverse cross-sectional area that is larger than a transverse cross-sectional area of the through-iris portion of the fixation member.

In one embodiment, the anchor structure adapted to be disposed in a posterior chamber of the eye has a generally elliptical transverse cross-sectional area. This is particularly useful when the anchor structure is formed prior to the IFIOL being placed in the eye. Such elliptical cross-sectional area facilitates placing the preformed anchor structure through the hole in the iris.

Methods of fixating an IOL, for example, the present IFIOLs, to an iris of an eye have been discovered. Such methods comprise inserting or placing the IOL into the eye, for example, through an incision in the eye. A distal segment of a fixation member of the IOL is directed through a through-hole extending through the iris such that a through-iris portion of the distal segment is disposed in the hole. The hole in the iris may be formed as part of the present methods, for example, employing conventional iridectomy techniques. An anchor structure of the distal segment is disposed or placed proximate to a side of the iris so that the anchor structure is adjacent the through-iris portion and the anchor structure is effective in fixating the intraocular lens to the iris.

In one embodiment, the anchor structure is a preformed anchor structure and the disposing step includes passing the preformed anchor structure through the through hole in the iris. Alternately, the present methods may include a step of changing the shape of an anchor portion of the distal segment in the eye to form the anchor structure. In this embodiment, the anchor portion may comprise a hydrophilic material and the changing step includes causing the anchor portion to absorb aqueous fluid, for example, from the eye, and form the anchor structure. The anchor portion may comprise an elastic memory material, and the changing step includes directing energy to the anchor portion, whereby the anchor portion absorbs the energy and the anchor structure is formed.

Each and every feature described herein, and each and every combination of two or more of such features is included with the scope of the present invention provided that the features included in such a combination are not mutually inconsistent.

These and other aspects of the present invention are apparent in the following detailed description and claims, particularly when considered in conjunction with the accompanying drawings in which like parts bear like reference numerals.

BRIEF DESCRIPTION OF THE DRAWINGS

Prior Art

FIG. 11 is a perspective view of an iris fixated intraocular lens before implantation in an eye according to an embodiment of the invention.

FIG. 12 is a side view of the iris fixated intraocular lens of FIG. 11 showing the vaulting of the optic relative to the fixation members.

FIG. 13 is a cross sectional view of the iris fixated intraocular lens of FIG. 11 implanted in an eye with preformed anchor structures at the ends at the intermediate portions of the fixation members.

DETAILED DESCRIPTION OF THE DRAWINGS

Figure 1:
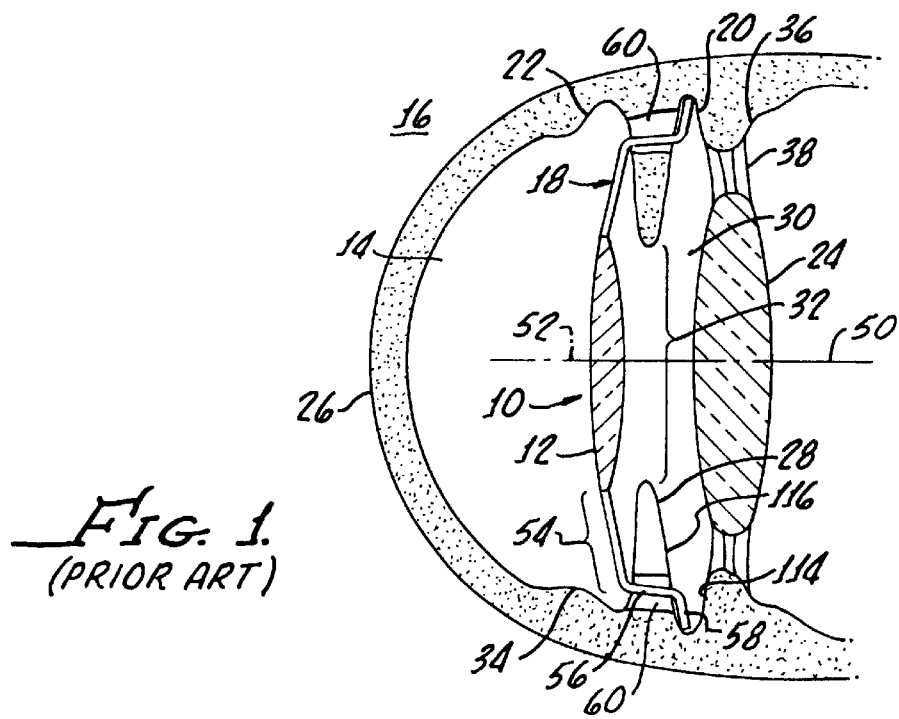
FIG. 1 is a cross-sectional view of an eye with a posterior/anterior intraocular lens implanted therein.
Figure 2:
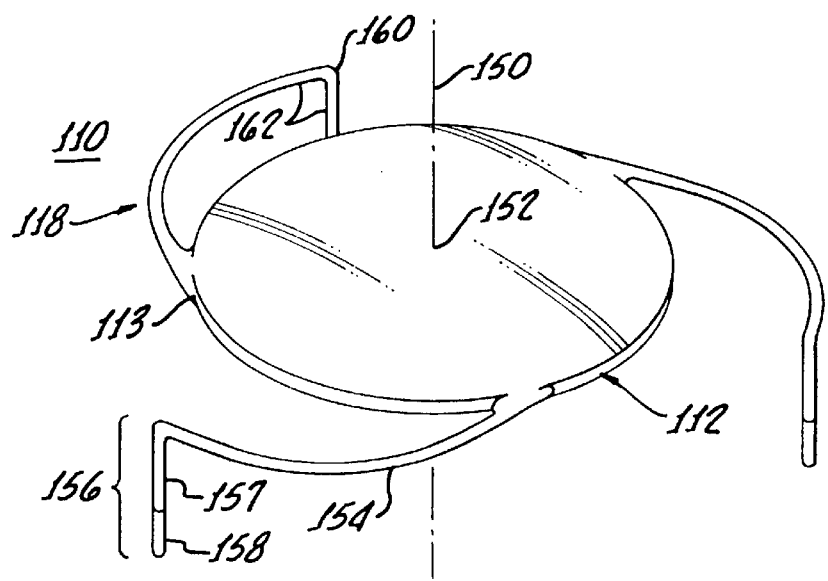
FIG. 2 is a perspective view of an iris fixated intraocular lens before implantation in an eye according to an embodiment of the invention.

Referring now to drawings, FIG. 2 shows an iris fixated intraocular lens ("IFIOL") 110 according to an embodiment of the invention in which the fixation members 118 come into contact with neither the sulcus nor the angle or ciliary band of the eye. The IFIOL 110 is comprised of an optic 112 and three fixation members or haptics 118. The optic 112 has an optical axis 150 extending through the center 152 of the optic and is generally normal to the optic. Each fixation member 118 has an elongated proximal segment 154 attached to the optic 112 near the periphery 113 of the optic. Each fixation member also has a distal segment 156 joined to the proximal segment 154, comprising a through-iris portion 157 and preferably terminating in a shape-changeable end 158.

Figure 3:
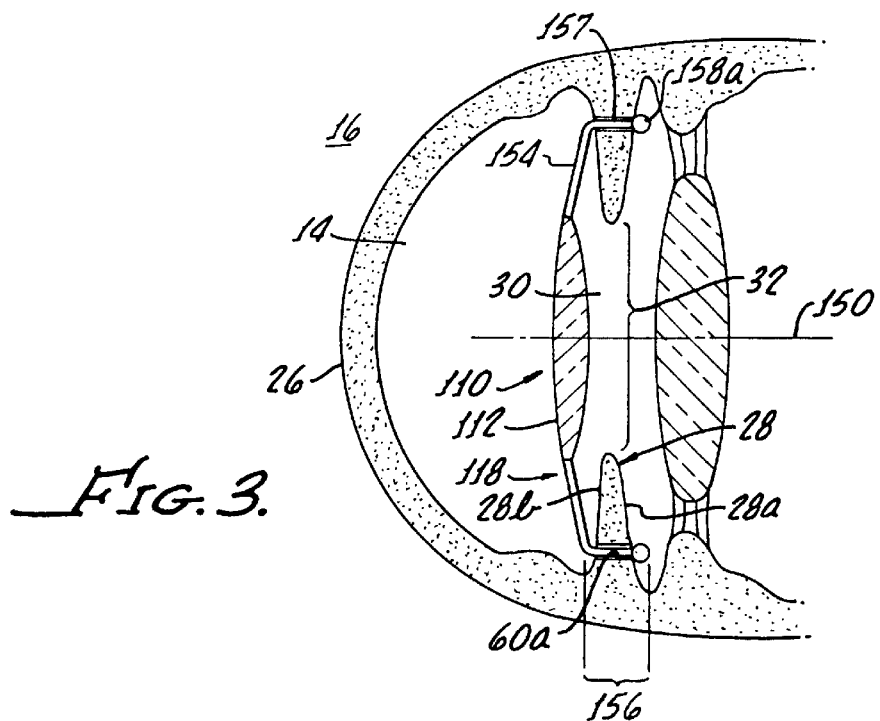
FIG. 3 is a cross sectional view of the iris fixated intraocular lens of FIG. 2 implanted in an eye with formed anchor structures of hydrogel at the ends of the fixation members.

The optic 112 in the shown embodiment is circular in plan and bi-convex (see FIG. 3). Other embodiments of the invention may have other configurations and shapes, such as convex-concave, bi-concave, planar-convex, planar concave, toric, and multifocal, for example, as disclosed in Portney U.S. Pat. No. 5,225,858, which is incorporated in its entirety herein by reference.

The optic 112 may be constructed of any commonly employed material or materials used for rigid optics, such as polymethylmethacrylate (PPMA), or commonly used for resiliently deformable or foldable optics, such as silicone polymeric materials, acrylic polymeric materials, hydrogel-forting polymeric materials, such as polyhydroxyethylmethacrylate, polyphosphazenes, polyurethanes, and mixtures thereof and the like. The particular material should form an optically clear optic 112 and exhibit biocompatibility in the environment of the eye 16, selection parameters for suitable intraocular lens materials are well known to those of skill in the art. See, for example, David J. Apple, et al., Intraocular Lenses. Evolution, Design, Complications, and Pathology, (1989) William & Wilkins. Foldable/deformable materials are particularly advantageous since optics made from such deformable materials may be rolled, folded or otherwise deformed and inserted into the eye through a small incision. It is preferred that the lens material has a refractive index allowing a relatively thin, and preferably flexible optic section, for example, having a thickness in the range of about 150 microns to about 1000 microns, and preferably about 150 microns or about 200 microns to about 500 microns. Further, the optic 112 may have a diameter of about 4.5 mm or less to about 6.6 mm or more, preferably about 5.0 mm to about 6.0 mm or about 6.5 mm, to avoid edge glare and be properly sized for placement in an adult human eye. In comparison, the distal segments 156 lie on a circle having a diameter of about 8 mm or less to about 11 mm or more, for example, about 9.5 mm, in an embodiment of the invention.

The fixation members 118 preferably are flexible yet sufficiently strong and resilient to hold the optic 112 in place yet permit the fixation members to flex in response to iris 28 movement. The fixation member may have a substantially circular transverse area diameter in a range of about 0.1 mm or less and about 0.2 mm or more, for example about 0.15 mm. Other embodiments of the invention may have fixation members with transverse areas of other shapes, such as oval, rectangular and the like. The fixation members 118 preferably are designed to flex so as to restrict or substantially eliminate movement of the optic 112 in the direction of the optical axis 150.

Optics and haptics in accordance with the present invention having the above-noted thicknesses and diameters can be produced using manufacturing methodologies which are conventional and well known in the IOL art.

The fixation members 118 may be formed integrally with the optic 102 or may be separately attached to the optic. The fixation members 118 may comprise any of a variety of materials which exhibit sufficient supporting strength and resilience, and which are substantially biologically inert in the intended in vivo or in-the-eye environment. Suitable materials for this purpose include, for example, polymeric materials such as polypropylene, PMMA, polycarbonates, polyatnides, polyimides, polyacrylates, 2-hydroxymethylmethacrylate, poly (vinylidene fluoride), polytetrafluoroethylene and the like; and metals such as stainless steel, platinum, titanium, tantalum, shape-memory alloys, e.g., nitinol, and the like.

More preferably, the fixation members 118 comprise a yen polymeric material, in particular selected from polypropylene, PMMA and polyimides, and especially polypropylene. The fixation members 118 can be produced using conventional and well known forming techniques. For example, the preferred polymeric fixation members can be formed in accordance with known thermoplastic polymer forming techniques, such as by injection molding or by extrusion. Further, selection parameters for suitable intraocular lens materials are well known to those skilled in the art.

Each fixation member proximal segment 154 defines an arc that extends generally normal to the optical axis 150. Each fixation member 118 has a discontinuity 160 where the proximal segment 154 joins the distal segment 156. In the shown embodiment of the invention, the proximal and distal segments 154 and 156 form a right angle 162, resulting in the iris-through portion 157 being parallel to the optical axis 150. Other embodiments of the invention may have the through-iris portion 157 oriented in a direction other than normal to the optical axis 150. Still other embodiments of the invention may have proximal segments 154 of any suitable configuration.

In the shown embodiment, the three fixation members 118 are symmetrical. Other embodiments of the invention may have non-symmetrical fixation members. In the shown embodiment of the invention, the fixation members 118 extend generally tangentially away from the optic periphery 113. Other embodiments of the invention may have fixation members 118 attached to the optic 112 which extend in a non-tangential fashion. Still other embodiments of the invention may have any number of fixation members of similar or different design. The shown embodiment of the invention has three fixation members 118 to increase stability of the IFIOL in the eye. Embodiments of the invention may have optics and fixation members that are essential unitary or may be assembled.

In an embodiment of the invention, the fixation members 118 are made of two or more materials. In a further embodiment of the invention, the shape-changeable end 158 may be comprised of a different material than the remainder of the fixation member 118.

Figure 4:
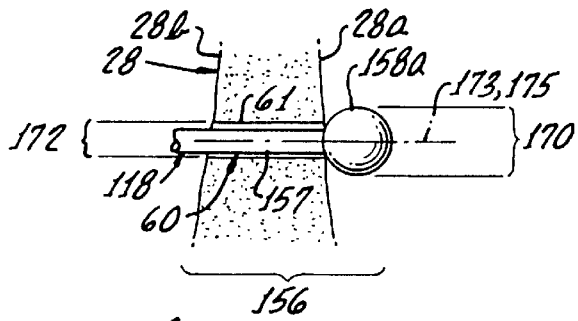
FIG. 4 is a detail view of the formed anchor structure of the iris fixated intraocular lens fixation member of FIG. 3.

Referring now to FIGS. 3 and 4 as well, the shape-changeable end 158 of the fixation member 118 is adapted to form an anchor structure 158a once the IFIOL 110 is implanted in the eye 16. The cross-sectional view shown in FIG. 3 is such that two of the three fixation members 118 are represented for clarity, although a straight cross-section would only show one of the three fixation members.

Prior to implantation, an iridectomy is performed to form the holes 60 that extend through the iris 28. The iridectomy is surgically formed using methods and instruments well known in the art. See, for example, the Apple et al, publication noted previously. The hole 60 is formed through the iris 28 so that the hole 60 receives the fixation member 118 and the fixation member fixably engages the IFIOL 110 to the iris. Fixed to the iris 28, the optic 112 of the IFIOL 110 is aligned with the pupil 32. In some embodiments of the invention, the fixation member 118 deforms the hole 60 while being inserted and in other embodiments the fixation member does not deform the hole, as described below.

The iridectomy facilitates fluid flow between the anterior chamber 14 and the posterior chamber 30. In a preferred embodiment of the invention, the holes 60 are near the outer periphery of the iris 28 because the radial positions of the holes do not substantially change during dilation and contraction of the iris compared to portions of the iris nearer the pupil. Other embodiments of the invention may have the holes 60 located other than the outer periphery of the iris 28. The holes 60 extend generally parallel to the optical axis 150. Other embodiments of the invention may have the holes 60 extending other than parallel to the optical axis 150. The holes 60 may be of any shape, including circular, oval, or slit.

In the shown embodiment of the invention, the IFIOL 110 is implanted such that the optic 112 and the proximal segments 154 of the fixation members 118 are disposed in the anterior chamber 14. With the optic 112 in the anterior chamber 14, there is a reduced opportunity for the IFIOL 110 to contact the natural lens 24 and initiate pupillary block and cataract formation. However, it should be understood that IFIOL 110 can be implanted in and function satisfactorily in an eye in which the natural lens has been extracted, e.g., using conventional techniques, or in an eye in which the natural lens has been extracted and replaced by an intraocular lens, e.g., of conventional design, located in the posterior chamber. Additionally, embodiments of the invention include IFIOLs adapted for the optic to be in the posterior chamber 30.

Further, the IFIOL 110 is implanted such that the fixation member distal segments 156 extend through the iris hole 60. More specifically, the through-iris portion 157 is disposed in the iris hole 60 and the formed anchor structure 158a is disposed in the posterior chamber 30 and proximate to an iris side 28a that defines the posterior chamber.

The formed anchor structure 158a has a diameter 170 that is greater than a diameter 172 of the hole 60. When the distal segment 156 was originally inserted through the hole 60, the shape-changeable end 158 (see FIG. 2) is able to pass through the hole without substantially deforming the walls 61 of the hole and potentially enlarging or tearing the hole.

In the shown embodiment of the invention, the shape-changeable end 158 comprises a hydrophilic material that absorbs aqueous fluid in the eye 16 and swells to form the bulbous anchor structure 158a after passing through the hole 60. The formed anchor structure 158a cannot pass back through the hole 60 due to its diameter 170 relative to the diameter 172 of the hole without deforming the iris hole walls 61. Further, as the anchor structure diameter 170 is greater than the hole diameter 172, the cross-sectional area of the anchor structure 158a is greater than the cross-sectional area of the hole 60. The cross-sectional area of the hole 60 is taken normal to the axis 173 of the hole. The cross-sectional area of the anchor structure 158a is taken normal to the centerline 175 of the fixation member at the anchor structure.

Embodiments of the invention include any suitable arrangement of any hydrophilic material that results in the formed anchor structure 158a that cannot pass through the hole 60 without deforming the walls 61 of the hole. The shown embodiment of the invention has a bulbous shape, but embodiments of the invention are not limited to hydrophilic material that forms a bulbous shape upon absorption of fluid. For example, the formed anchor structure of other embodiments may be any rotational shape, partial rotational shape, or non-rotational shape that has a width greater than a width of the hole 60, whereby the anchor structure cannot be directed through the hole without distorting the hole.

It is understood that "width" is a length of the span of the opening of the hole 60 or the anchor portion in a direction normal to the axis of the hole. In the case of a circular anchor structure and a circular opening of the hole 60, the width is a diameter. In the cases of non-circular holes and anchor structures, the width is any span. Additionally, when the IFIOL 110 is installed in the eye 16, the widths of respective anchor structures and holes are oriented such that the anchor structure cannot be directed through the hole without distorting the hole.

Examples of hydrophilic materials of the shape-changeable-end 158a of embodiments of the invention include acid or base treated polymeric materials. The shape-changeable end 158a may comprise a hydrogel-forming polymeric material, either entirely or a portion, such as a coating on a non-hydrogel-forming component of the shape-changeable end. Examples of suitable hydrogel-forming polymeric materials include poly(2-hydroxyethyl methacrylate) and a copolymer of ethyl methacrylate and N,N-dimethylacrylamide.

The shape-changeable end 158a may be the result of treating the end of the fixation member 118 with acid or base, which reacts with the fixation member material, such as PMMA or other suitable material effective when treated with an acid and/or base to provide a useful hydrophilic material, to form a hydrophilic outer layer. In further embodiments of the invention, the hydrophilic material is coated with a dissolvable or otherwise removable or breachable biocompatible sealer to temporarily inhibit the material absorbing the fluid, thereby providing a period of time before the material swells to form the anchor structure.

Figure 5:
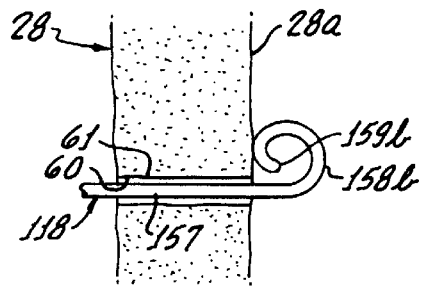
FIGS. 5 and 6 are detail views of formed anchor structures of the iris fixated intraocular lens made of elastic memory material.

Referring now to FIG. 5 as well, in another embodiment of the invention, the shape-changeable end 158 of the fixation member 118 is comprised of an elastic memory material that changes from a linear state to a curled state to form the anchor structure 158b. Attention is drawn to the curled formed anchor 158b structure having an end 159b that is not in contact with the iris side 28a, which reduces irritation to the iris 28. The formed anchor structure 158b is also curled in a direction parallel to the through-iris portion 157.

Figure 6:
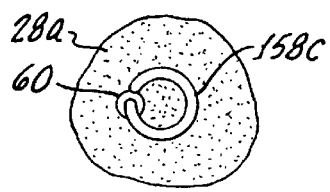

Referring now to FIG. 6, an anchor structure 158c is formed of elastic memory material that forms a curl that is normal to the direction of the through-iris portion (not shown). Other embodiments of the invention may include shape-changeable ends of elastic memory material that form any suitable formed anchor structure i.e., an anchor structure that cannot be directed through the iris hole 60 without deforming the iris hole walls 61 or an anchor structure having a width greater than a width of the iris hole. In a preferred embodiment of the invention, the formed anchor structures 158b and 158c are the result of pinpoint heating of the shape-changeable end 158 by use of an appropriate energy source, such as a laser. The shape-changeable end 158 absorbs the energy and forms the anchor structure.

In an embodiment of the invention, the elastic memory material is a polymeric material having a glass transition temperature (Tg) of at least about 40° C. to about 45° C., preferably in the range of about 40° C. to about 80° C., and more preferably in the range of about 45° C. to about 60° C. The polymeric material should be such that the Tg is sufficiently high to avoid any changes in the material caused by the physiological environment of the eye. On the other hand, the Tg of the polymeric material should not be excessively high, since heating the material to excessively high temperatures may result in damage or injury to the eye. Suitable polymeric materials are disclosed in the Weinschenk, III et al U.S. Pat. No. 5,567,365, which is incorporated herein in its entirety by reference.

The elastic memory polymeric material, as well as the material from which the optic is derived, used should be compatible with the eye 16 so implantation of the IFIOL 110 does not cause any significant harm or damage to the eye. Further, the optic 112 and the fixation members 118 may also comprise the polymeric material.

Typical examples of useful elastic memory polymeric materials include homopolymers of and copolymers derived from methyl methacrylate, n-hexyl acrylate, ethyl methacrylate, ethyl acrylate, 3,3-dimethylbutyl methacrylate, isobutyl methacrylate, cyclohexyl methacrylate, sec-butyl methacrylate, benzyl methacrylate, 4-tert-butylphenyl acrylate, 4-ethoxycarbonyl phenyl acrylate, 2-methoxycarbonyl phenyl acrylate, 3-methoxycarbonyl phenyl acrylate, 4-methoxycarbonyl phenyl acrylate, phenyl acrylate, and the like and mixtures thereof. Elastic memory polymeric materials other than acrylic-based materials, such as certain acrylamides, polyolefins, polycarbonates and the like may be used in embodiments of the invention. Copolymers are particularly useful as they may be custom formulated to obtain specific Tg and other properties desired.

Figure 7:
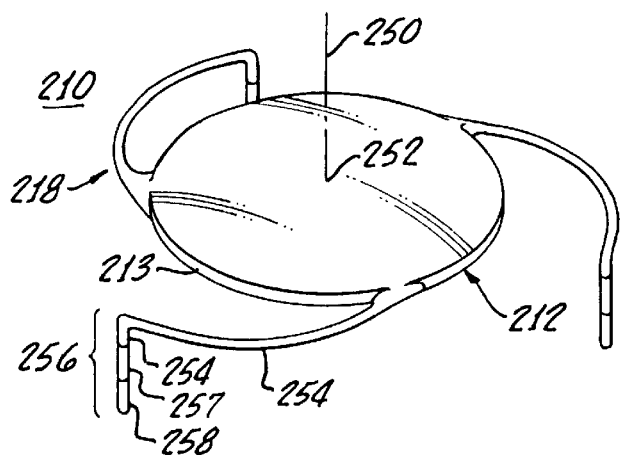
FIG. 7 is a perspective view of an iris fixated intraocular lens before implantation in an eye according to an embodiment of the invention.
Figure 8:
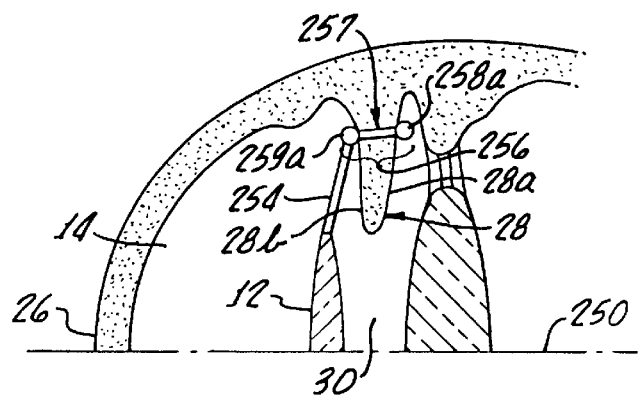
FIG. 8 is a cross sectional view of the iris fixated intraocular lens of FIG. 7 implanted in an eye with formed anchor structures at the ends and intermediate portions of the fixation members.

FIGS. 7 and 8 show alternative IFIOL 210 of the present invention. Alternative IFIOL 210 is structurally and functionally similar to IFIOL 110 except as expressly described herein. Components of alternative IFIOL 210 which correspond to components of IFIOL 110 are identified by the same reference number increased by 100.

Referring now to FIG. 7, IFIOL 210 is comprised of an optic 212 and three fixation members or fixation members 218. The optic 212 has an optical axis 250 extending through the center 252 of the optic and is generally normal to the optic. Each fixation member 218 has a proximal segment 254 attached to the optic 212 near the periphery 213 of the optic. Each fixation member also has a distal segment 256 joined to the proximal segment 254, comprising a through-iris portion 257, terminating in a shape-changeable end 258, and having a shape-changeable portion 259 between the through-iris portion and the proximal segment.

The IFIOL 210 is similar to the IFIOL 110 described above but for the shape-changeable portion 259. The shape-changeable portion 259 is adapted to form an additional anchor structure 259a once the IFIOL 210 is implanted in the eye 16 as shown in FIG. 8.

The formed additional anchor structure 259a is adapted to be disposed in the proximity of the iris side 28b, which defines the anterior chamber 14 and opposes iris side 28a. The anchor structure 258a and the additional anchor structure 259a straddle the iris 28 to hold the through-iris portion 257 in the iris hole 60. Other embodiments of the invention may include any shape-changeable end 258 and shape-changeable portion 259 of elastic memory material or hydrogel-forming polymeric material that forms any suitable formed anchor structure i.e., an anchor structure that cannot be directed through the iris hole 60 without deforming the iris hole walls 61 or an anchor structure having a width greater than a width of the iris hole.

In embodiments of the invention, the shape-changeable end 258 and the shape-changeable portion 259 may comprise any of the materials discussed above in connection with the shape-changeable end 158 of IFIOL 110. It also follows that the anchor structure 258a and the additional anchor structure 259a may be formed in the same manner as discussed above in connection with the shape-changeable end 158. In the embodiment of the invention in which the shape-changeable portion 259 is comprised of an elastic memory material, the formed additional anchor structure 259a is suitable as an intermediately positioned component of the fixation member 218, as opposed to the terminally positioned anchor structure 258a.

Figure 9:
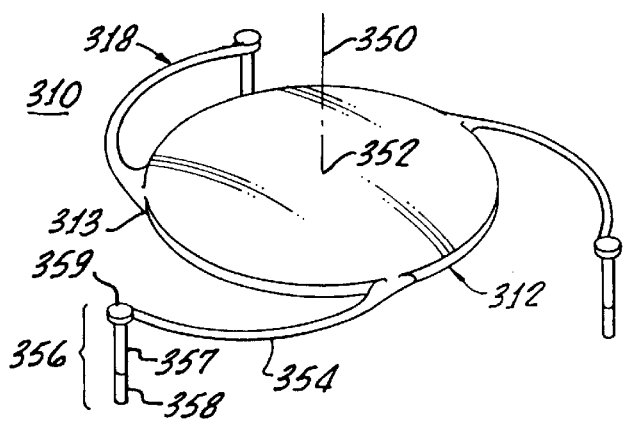
FIG. 9 is a perspective view of an iris fixated intraocular lens before implantation in an eye according to an embodiment of the invention.
Figure 10:
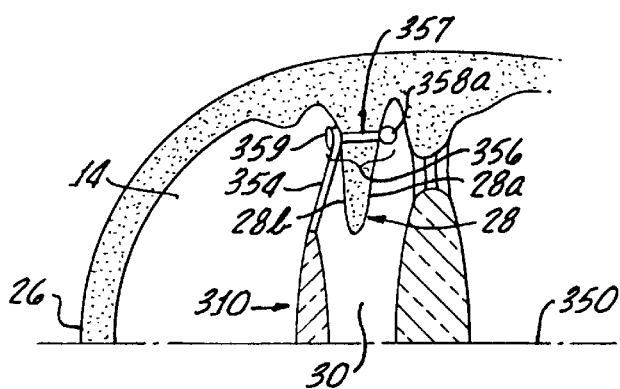
FIG. 10 is a cross sectional view of the iris fixated intraocular lens of FIG. 9 implanted in an eye with formed anchor structures at the ends and preformed anchor structures at the intermediate portions of the fixation members.

FIGS. 9 and 10 show additional IFIOL 310 of the present invention. Additional IFIOL 310 is structurally and functionally similar to IFIOL 110 and IFIOL 210 except as expressly described herein. Components of additional IFIOL 310 which correspond to components of IFIOL 110 and IFIOL 210 are identified by the same reference number increased by 200 and 100, respectively.

Referring now to FIG. 9, IFIOL 310 is comprised of an Hoptic 312 and three fixation members 318. The optic 312 has an optical axis 350 extending through the center 352 of the optic and is generally normal to the optic. Each fixation member 318 has a proximal segment 354 attached to the optic 312 near the periphery 313 of the optic. Each fixation member also has a distal segment 356 joined to the proximal segment 354, comprising a through-iris portion 357, terminating in a shape-changeable end 358, and having a preformed anchor structure 359 between the through-iris portion and the proximal segment.

Referring now to FIG. 10, the IFIOL 310 is similar to the IFIOL 210 described above but for the preformed anchor structure 359 replacing the shape-changeable portion 259. The preformed anchor structure 359 does not pass through the hole 60 in the iris 28 and, therefore, has a width greater than a width of the iris hole or otherwise cannot pass through the iris hole without deforming the iris hole wall 61. The resulting implanted IFIOL 310 is similar to the implanted IFIOL 210.

FIGS. 11–15 show further IFIOL 410 of the present invention. Further IFIOL 410 is structurally and functionally similar to IFIOLs 110, 210 and 310 except as expressly described herein. Components of further IFIOL 410 which correspond to components of IFIOLs 110, 210, and 310 are identified by the same reference number increased by 300, 200, and 100, respectively.

Referring now to FIG. 11, in an embodiment of the invention. IFIOL 410 is comprised of an optic 412 and three fixation members 418. The optic 412 has an optical axis 450 extending through the center 452 of the optic and is generally normal to the optic. Each fixation member 418 has a proximal segment 454 attached to the optic 412 near the periphery 413 of the optic. Each fixation member 418 also has a distal segment 456 joined to the proximal segment 454, comprising a through-iris portion 457, terminating in a preformed anchor structure 458, and having another preformed anchor structure 459 between the through-iris portion and the proximal segment.

Referring now to FIGS. 12 and 13, the IFIOL 410 is shown with an optical plane 480 that is normal to the optical axis 450. The fixation members 418 extend posteriorly from the optical plane 480, such that the lens 412 is vaulted. The posteriorly positioning of the fixation members 418 result in the fixation members and the optic 412 being supported in a spaced apart position to the iris 28. This provides the advantage of mitigating inflammation of the iris 28 by reducing or eliminating abrasion of the fixation members 418 against the iris surface 28b.

Figure 14:
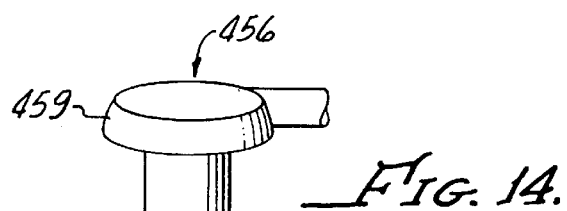
FIGS. 14 and 15 are detail views of anchor portions of fixation members of the iris fixated intraocular lens of FIG. 11 according to embodiments of the invention.
Figure 15:
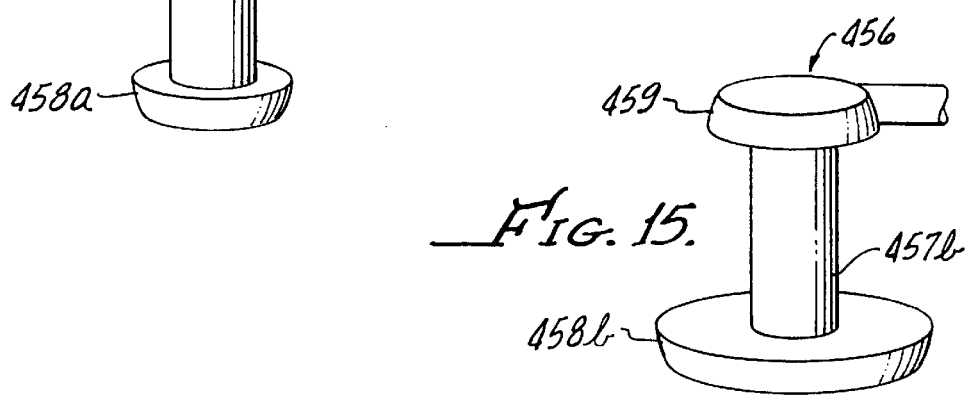

Referring now to FIGS. 14 and 15, embodiments of the invention have a distal segment 456 with a circular preformed anchor structure 458a and an ellipsoidal preformed anchor structure 458b. The ellipsoidal preformed anchor structure 458b is relatively easy to pass through the iris hole and, once through the hole, remains posterior to the iris. In one embodiment, the through iris portion 457b, or at least that part of the through iris portion which is directly adjacent to ellipsoidal preformed anchor structure 458b, may be made of an elastic memory material, as described elsewhere herein. The through iris portion 457b is produced and structured so that the ellipsoidal anchor structure 458b can be passed through a hole in the iris and, afterward, because of the elastic memory characteristic of the through iris portion, is effectively twisted to rotate the anchor structure 458b, for example, through an angle of about 90°, to make it more difficult for the anchor structure to pass through the iris hole. Thus, the anchor structure 458b is more securely positioned posterior of the iris and the IOL is more securely fixated to the iris. This is but one example of embodiments of the present invention in which combinations of preformed anchor structures and elastic memory materials can advantageously be used together. Other embodiments of the invention may have preformed anchor structures 458 and 459 of any suitable shape, including shapes that minimize contact with the iris 28 and shapes that permit fluid exchange between the two chambers through the iris through-hole (see FIG. 13).

Figure 16:
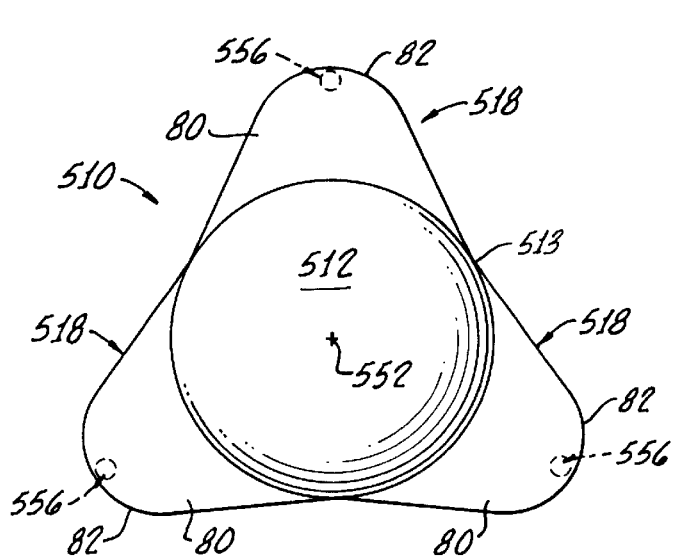
FIG. 16 is a front view of an alternate iris fixated intraocular lens before implantation in an eye according to an embodiment of the present invention.
Figure 17:
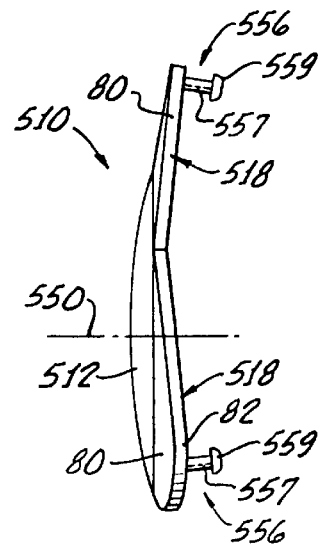
FIG. 17 is a side view of the iris fixated intraocular lens of FIG. 16.

FIGS. 16 and 17 show alternate IFIOL 510 in accordance with the present invention. Alternate IFIOL 510 is structurally and functionally similar to the IFIOLs 110, 210, 310 and 410 except as expressly described herein. Components of alternate IFIOL 510 which correspond to components of IFIOLs 110, 210, 310 and 410 are identified by the same reference number increased by 400, 300, 200 and 100, respectively.

The primary difference between IFIOL 510 and the earlier illustrated IFIOLs relates to the structure of the fixation members 518.

Thus, referring now to FIGS. 16 and 17, alternate IFIOL 510 is comprised of an optic 512 and three fixation members 518 equidistantly spaced apart around the circular periphery 513 of the optic. The optic 512 has an optical axis 550 extending through the center 552 of the optic and is generally normal to the plane of the optic.

Each fixation member has a plate or tab element 80 attached to the optic 512 near the periphery 513 of the optic. The plate elements 80 are adapted to be placed or disposed in the anterior chamber of the eye when the IFIOL 510 is fixated to the iris of the eye. In addition, each fixation member 518 has a distal segment 556 joined to plate element 80 near the distal end 824 of the plate element. Each distal segment 556 includes a through-iris portion 557, terminating in a preformed anchor structure 559. The plate elements 80 are shaped so that the distal end 82 is slightly posterior of the regions of the plate elements 80 directly attached to the optic 512. This shaping of the plate elements 80 allows the distal end 82 to act as or be considered another preformed anchor structure which facilitates maintaining the through-iris portion 557 of each of the fixation members 518 in the iris hole. It is to be understood that the preformed anchor structures 559 can be replaced by an anchor structure which is formed only after the IFIOL 510 is in the eye, for example, as described elsewhere herein. In addition, the number of fixation members 518 is not critical to the present invention. However, it is preferred that at least three, and more preferably three or four, fixation members 518 be provided.

In contrast to the elongated proximal segments of the fixation members of the earlier illustrated IFIOLs, the plate elements 80 are relatively stronger and provide enhanced stability. However, the plate elements 80, like the optic 512, preferably are made of a deformable material so that the optic and plate elements can be rolled, folded or otherwise deformed for insertion into an eye through a small incision.

The relatively strong plate elements 80 provide substantial benefits. For example, such plate elements 80 facilitate, that is make easier, the placement of IFIOL 510 into the eye. Such placement in the eye requires less time and/or surgical technique and/or is less traumatic to the patient and/or is less stressful to the surgeon, relative to a substantially identical IFIOL in which the plate elements 80 are replaced by thin filament-like members. Additionally, after IFIOL 510 is in the eye, the plate elements 80 are effective in stabilizing the optic 512 against unwanted movement, for example, which can cause distortion in the patient's vision.

The plate elements 80 can be made of any suitable material, many examples of which have been disclosed previously herein. The plate elements 80 can be made separately from the optic 512 and then bonded or secured to the optic, or the plate elements and the optic can be made together as a single piece.

In a preferred embodiment of the invention, the iridectomy results in through-iris holes that match the distal segments of the IFIOL to be implanted in the eye. Further, the IFIOL preferably is designed to prevent dislodgement of the fixation members from the iris, and not to interfere with the natural crystalline lens, zonules, or any other part of the eye. If desired or necessary, the present IFIOL may be removed from the eye and replaced with another IFIOL, a PACL, an AIOL, a PIOL, or another eye implant device.

In embodiments of the invention, at least the terminal ends of the fixation members may be made of nontransparent material, such as PMMA with a dye, to facilitate observing the fixation member placement through the iris hole 60 under proper illumination. In a preferred embodiment of the invention, the remainder of the fixation members are made from visually transparent material to minimize cosmetic issues.

Enlargement of one or more of the iris holes 60, for example, after the IFIOL is implanted, may be performed to increase fluid flow between the anterior and posterior chambers 14 and 30 of the eye 16. In other embodiments of the invention, the formed or preformed anchor structures are adapted to permit fluid flow through the iris holes 60.

Embodiments of the invention include IFIOLs that are implanted to address different refraction deficiencies, such as hyperopia, astigmatism, myopia, and presbyopia.

In preferred embodiments of the invention, the fixation members and anchor structures, both preformed and formed in the eye, are adapted to avoid damaging the iris tissue during insertion, fixation, and removal of the IFIOL from the eye.

While the description above refers to particular embodiments of the present invention, it will be understood that many modifications may be made without departing from the spirit thereof. For example, while FIG. 3 shows the IFIOL 110 implanted in the eye 16 with a natural lens 34, other embodiments of the invention may have an IFIOL implanted in an eye without a natural lens, or with a replacement lens. Another example is a fixation member having a distal end segment comprising both hydrogel material and elastic memory material. Further, aspects of the invention may have combinations of the above described embodiments although these combinations may not be explicitly described.

While this invention has been described with respect to various specific examples and embodiments, it is to be understood that the invention is not limited thereto and that it can be variously practiced within the scope of the following claims.

What is claimed is:

1. A method for fixating an intraocular lens to an iris of an eye including an anterior chamber in front of the iris, the intraocular lens comprising an optic structured Lo be disposed substantially completely in the anterior chamber and a fixation member joined to the optic, the method comprising the steps of:
   inserting the intraocular lens into the eye so that the optic is disposed substantially completely in the anterior chamber;
   directing a distal segment of the fixation member of the intraocular lens through a through-hole extending through the iris such that a through-iris portion of the distal segment is disposed in the hole; and
   disposing an anchor structure of the distal segment proximate to a side of the iris, whereby the anchor structure is effective in fixating the intraocular lens to the iris, the disposing step including changing the shape of an anchor portion of the distal segment in the eye to form the anchor structure.

2. The method of claim 1, wherein the anchor portion comprises a hydrophilic material and the changing step includes causing the anchor portion to absorb aqueous fluid and form the anchor structure.

3. The method of claim 1, wherein the optic is deformed during at least a portion of the inserting step.

4. The method of claim 1, wherein the anchor portion comprises an elastic memory material, and the changing step comprises directing energy to the anchor portion, whereby the anchor portion absorbs the energy and the anchor structure is formed.

5. An intraocular lens for fixation to an iris of an eye, the iris having a side and a hole extending from the iris side and through the iris. the intraocular lens comprising:
   an optic; and
   at least one fixation member joined to the optic and comprising a distal segment including a through-iris portion adapted to extend through the iris hole and an anchor portion comprising a hydrophilic material adapted to form an anchor structure after the intraocular lens is placed in the eye, the anchor structure positioned to be disposed proximate to the iris side so as to be effective in fixating the intraocular lens to the iris.

6. The intraocular lens of claim 5, wherein the hydrophilic material comprises an acid-treated polymer or a base-treated polymer.

7. The intraocular lens of claim 5, wherein the hydrophilic material comprises a hydrogel-forming polymeric material.

8. An intraocular lens for fixation to an iris of an eye, the iris having a side and a hole extending from the iris side and through the iris, the intraocular lens comprising:
   an optic, and
   at least one fixation member joined to the optic and comprising a distal segment including a through-iris portion adapted to extend through the iris hole and an anchor portion having or adapted to have an anchor structure positioned to be disposed proximate to the iris side in a posterior chamber of the eye so as to be effective in fixating the intraocular lens to the iris, the anchor structure having a generally elliptical transverse cross-sectional area.

9. A method for fixating an intraocular lens to an iris of an eye, the method comprising the steps of:
   inserting the intraocular lens into the eye;
   directing a distal segment of the fixation member of the intraocular lens through a through-hole extending through the iris such that a through-iris portion of the distal segment is disposed in the hole; and
   disposing an anchor structure of the distal segment proximate to a side of the iris, whereby the anchor structure is effective in fixating the intraocular lens to the iris, the disposing step including changing the shape of an anchor portion of the distal segment in the eye to form the anchor structure, the anchor portion comprising a hydrophilic material and the changing step including causing the anchor portion to absorb aqueous fluid and form the anchor structure.

10. An intraocular lens for fixation to an iris of an eye including an anterior chamber in front of the iris, the iris having a side and a hole extending from the iris side and through the iris, the intraocular lens comprising:
   an optic structured to be disposed substantially completely in the anterior chamber, the optic is deformable so that the intraocular lens can be inserted into an eye through a small incision; and
   at least one fixation member joined to the optic and comprising a distal segment including a through-iris portion adapted to extend through the iris hole and an anchor portion having or adapted to have an anchor structure positioned to be disposed proximate to the iris side in a posterior chamber of the eye so as to be effective in fixating the intraocular lens to the iris, the anchor structure having a generally elliptical transverse cross-sectional area.

* * * * *

UNITED STATES PATENT AND TRADEMARK OFFICE
CERTIFICATE OF CORRECTION

PATENT NO. : 6,478,821 B1
DATED : November 12, 2002
INVENTOR(S) : Laguette et al.

It is certified that error appears in the above-identified patent and that said Letters Patent is hereby corrected as shown below:

Column 5,
Line 66, "forting" should read -- forming --.

Column 6,
Line 4, "selection" should read -- Selection --.
Line 48, "polyatnides" should read -- polyamides --.
Line 53, delete "yen".

Column 10,
Line 58, "Hoptic" should read -- Optic --.

Column 13,
Line 40, "structured Lo be" should read -- structured to be --.

Column 14,
Line 35, "the fixation member" should read -- a fixation member --.

Signed and Sealed this

Third Day of June, 2003

JAMES E. ROGAN
*Director of the United States Patent and Trademark Office*